United States Patent [19]
Hanover et al.

[11] Patent Number: 6,104,780
[45] Date of Patent: Aug. 15, 2000

[54] MOBILE BI-PLANAR FLUOROSCOPIC IMAGING APPARATUS

[75] Inventors: Barry Hanover; Larry Anderton; Steven Curtis, all of Salt Lake City, Utah

[73] Assignee: OEC Medical Systems, Inc., Salt Lake City, Utah

[21] Appl. No.: 08/977,311

[22] Filed: Nov. 24, 1997

[51] Int. Cl.[7] .................................................. H05G 1/70
[52] U.S. Cl. ............................ 378/92; 378/101; 378/197
[58] Field of Search ................................. 378/41, 42, 92, 378/101

[56] References Cited

U.S. PATENT DOCUMENTS

| | | |
|---|---|---|
| 3,424,901 | 1/1969 | Kok . |
| 3,549,885 | 12/1970 | Andersson . |
| 3,617,749 | 11/1971 | Massiot . |
| 4,541,293 | 9/1985 | Caugant . |
| 4,884,293 | 11/1989 | Koyama . |
| 4,887,287 | 12/1989 | Cobben . |
| 4,918,716 | 4/1990 | Hahn . |
| 5,095,501 | 3/1992 | Kobayashi . |
| 5,107,528 | 4/1992 | Asahina et al. ............................ 378/41 |
| 5,367,554 | 11/1994 | Kobayashi . |
| 5,386,453 | 1/1995 | Harrawood . |
| 5,515,416 | 5/1996 | Siczek ..................... 378/197 |

Primary Examiner—Craig E. Church
Attorney, Agent, or Firm—Thorpe, North & Western, LLP

[57] ABSTRACT

A mobile, bi-planar fluoroscopic imaging apparatus has first and second imaging systems disposed on first and second C-arms. The C-arms are preferably disposed on wheeled bases allowing for movement from one place to another. Alternatively, the first C-arm is large and disposed on a wheeled base while the second C-arm is smaller and disposed on the first C-arm such that it nests. A controller sends trigger pulses to the imaging systems causing the systems to alternate operation. Alternatively, the first and second systems are configured in a master/slave relationship with the master system sending triggering pulses to the slave. A display continuously displays the images produced by the imaging systems such that an image produced by the first system is displayed while the second system operated to produce an image and vis versa. A storage device stored the images as they are produced and later delivers the images to the display for viewing.

21 Claims, 5 Drawing Sheets

MOBILE BI-PLANAR FLUOROSCOPIC IMAGING APPARATUS

BACKGROUND OF THE INVENTION

1. Field of the Invention

The present invention relates to a mobile, bi-planar x-ray imaging apparatus. More particularly, the present invention relates to a x-ray imaging apparatus having two imaging systems each disposed on two, independently movable C-arms with a control system in communication with both imaging systems such that they alternate taking x-rays.

2. Prior Art

It is often desirable to take X-rays of a patient from a number of different positions, preferably without the need for frequent repositioning of the patient. It is preferable that the X-ray support structure not unduly encumber the space immediately surrounding the patient to enable a physician to treat or otherwise attend to the patient without the need to repeatedly remove and replace the X-ray equipment. Mobile C-arm X-ray diagnostic equipment has been developed to meet these needs and has become well known in the medical art of surgical and other interventional procedures.

A C-arm refers generally to an elongate C-shaped member terminating in opposing distal ends of the "C" shape. An X-ray source and an image receptor are typically mounted at or near the distal ends, respectively, of the C-arm in opposing orientation, with the C-arm supported in a suspended position. The space within the C-shape of the arm provides room for the physician to attend to the patient substantially free of interference from the X-ray support structure. The support structure usually rests upon wheels which enable the C-arm to be wheeled from room to room, and along the length of a patient while the physician operates or examines, ensuring that devices such as cardiac catheters, long bone nails, etc. are properly positioned during the procedure.

The C-arm is usually mounted so as to enable rotational movement of the arm in two degrees of freedom, i.e. about two perpendicular axes in a spherical motion. More specifically, the C-arm is slidably mounted to the support structure to enable orbiting rotational movement of the C-arm about its center of curvature, thereby permitting the X-ray source and the image receptor to be selectively oriented vertically, horizontally, or somewhere in between. The C-arm is also laterally rotatable, i.e. in a perpendicular direction relative to the orbiting direction to enable selectively adjustable positioning of the X-ray source and receptor relative to both the width and length of the patient. The spherically rotational aspects of C-arm apparatus allow the physician to take X-rays of the patient at an optimal angle as determined with respect to the particular anatomical condition being imaged.

Designers and manufacturers of C-arm equipment are faced with a number of challenges. The support structure used to support and rotate a C-arm in its various suspended positions must be strong enough to withstand tremendous torsional, tensile and compressive stresses. The support structure must also be heavy enough and have a large enough footprint to avoid tipping over upon lateral rotation of the C-arm, which causes the center of gravity to shift dramatically. There have been previous attempts to provide C-arm support structure to solve the problems mentioned above. Exemplary of such prior art attempts is U.S. Pat. No. 4,955,046 (issued to Siczek et al. on Sep. 4, 1990) which discloses a C-arm apparatus. A wheeled support cart includes a rotatable L-arm upon which a C-arm is slidably mounted. The L-arm thus provides rotational movement of the C-arm in two degrees of freedom.

In addition, it is often desirable to take X-rays of a patient from a number of different angles, preferably in quick succession and without repositioning the C-arm. Such a configuration is often referred to as bi-planar imaging and allows an object to be viewed in two planes simultaneously. The two X-ray beams emitted from the two X-ray tubes may cross at an iso-center. Bi-planar imaging is useful for checking a catheter position, a balloon status or performing a digital subtraction run.

Bi-planar imaging may be accomplished in several ways. One way is by using two independent imaging systems, or two C-arms. U.S. Pat. No. 4,884,293 issued Nov. 28, 1989, to Koyama discloses a dual imaging system with one imaging system being mounted to the floor and the other being mounted to the ceiling. One disadvantage of this system is that it is permanently mounted to the floor and ceiling. Thus, the system cannot be moved about a hospital as needed. Another disadvantage of this system is that, although the C-arms are coordinated, the imaging systems operate independently of one another. Thus, the images produced are not coordinated.

Another configuration for obtaining bi-planar imaging is slidingly nesting one C-arm in another. U.S. Pat. No. 5,515,416 issued May 7, 1996, to Siczek et al. discloses a dual imaging system with one C-arm being mounted to the floor and the other C-arm being slidingly disposed on the first C-arm. One disadvantage of this system is that the two imaging systems may not be moved independently of one another. Thus, the positioning of the second imaging system is limited by the position of the first. Another disadvantage is that it is permanently mounted to the floor. Thus, it cannot be moved about a hospital. A further disadvantage is that the two images must share a common iso-center because they are nested.

Another configuration for obtaining bi-planar imaging is disposing the imaging systems in a ring, as opposed to C-arms. U.S. Pat. No. 3,549,885 issued Dec. 22, 1970, to Andersson discloses a dual imaging system with both imaging systems being mounted perpendicularly in a rotatable ring. One disadvantage with this system is that the bi-planar images are always disposed at a fixed, perpendicular angle with respect to each other.

Another configuration for obtaining bi-planar imaging is disposing the imaging systems on a G-arm, as opposed to C-arms. U.S. Pat. No. 5,095,501 issued Mar. 10, 1992, to Kobayashi discloses a dual imaging system with both imaging systems being mounted perpendicularly in a G-shaped arm. Like the ring configuration above, one disadvantage of this system is that the bi-planar images are always disposed at a fixed, perpendicular angle with respect to each other.

Furthermore, it is often desirable to view X-rays in real time and to save or store X-rays taken of a patient for later review. It is difficult to operate both imaging systems at the same time because both systems typically operate independently. In addition, if both systems operate at the same time, the two X-ray beams cause a blurred picture and expose the subject to excessive radiation due to scattering.

Therefore, it would be advantageous to develop a mobile, bi-planar imaging system with independently movably imaging systems capable of being moved and capable of various bi-planar angles. It would also be advantageous to develop a bi-planar imaging system with a control system to automatically operate the imaging systems by alternately operating each imaging system. It would also be advantageous to develop a bi-planar imaging system capable of real time display and real time storage of images.

OBJECTS AND SUMMARY OF THE INVENTION

It is an object of the present invention to provide a mobile bi-planar imaging system that is capable of various bi-planar angles.

It is another object of the present invention to provide a bi-planar imaging system with a control system for automatically operating the imaging systems in an alternating sequence.

It is yet another object of the present invention to provide a bi-planar imaging system with real time display and real time image storage.

These and other objects and advantages of the present invention are realized in a mobile, bi-planar imaging apparatus having first and second imaging systems disposed on first and second C-arms and having a controller to cause the imaging systems to alternately operate to produce a series of sequential images. The first imaging system has a first X-ray source and a first image receptor disposed on opposing ends of a first C-shaped arm. The second imaging system likewise has a second X-ray source and a second image receptor disposed on opposing ends of a second C-shaped arm. The first and second C-arms are preferably movably disposed on wheeled bases. Thus, the apparatus may be moved about a facility, such as a hospital, and moved about a patient.

Alternatively, the first C-arm is large and moveably disposed on a wheeled base. The second C-arm is small and movably disposed on the first C-arm such that it may nest within the first C-arm.

Alternatively, the first C-arm is large and moveably disposed on a first wheeled base. The second C-arm is small and also moveably disposed on a second wheeled base.

The apparatus also has a controller coupled to the first and second imaging systems to cause the imaging systems to alternate operation. The imaging systems will typically be positioned such that the X-ray beams produced will cross. If operated at the same time, the crossing beams may cause blurred images and excessive radiation exposure to the patient. Therefore, the controller alternates the operation of the image systems. The controller may be an external controller or the imaging systems may be configured in a master/slave relationship. The controller, or master, sends a triggering pulse causing the imaging system to operate.

The apparatus also has a display for displaying the images produced by the imaging system. The display may be two monitors each displaying images from the first and second systems, respectively, or may be a single monitor displaying images from both systems simultaneously, such as a split screen. The display displays the images from the two systems continuously. Thus, an image produced by the first system is displayed while the second system is operating. Likewise, an image produced by the second system is displayed while the first system operates.

The apparatus has a storage device coupled to the first and second imaging systems for storing images as they are produced. The storage device later delivers the images to the display for viewing.

The process of the present invention includes the steps of providing first and second imaging systems for producing images in first and second planes; operating the first system to produce an image defining a first frame of the first system; displaying the first frame of the first system; storing the first frame of the first system; operating the second system to produce an image defining a first frame of the second system; displaying the first frame of the second system; storing the first frame of the second system; and then repeating the steps of operating the systems and displaying and saving the images. The image of one system is displayed continuously while the other system operates to produce an image.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1:
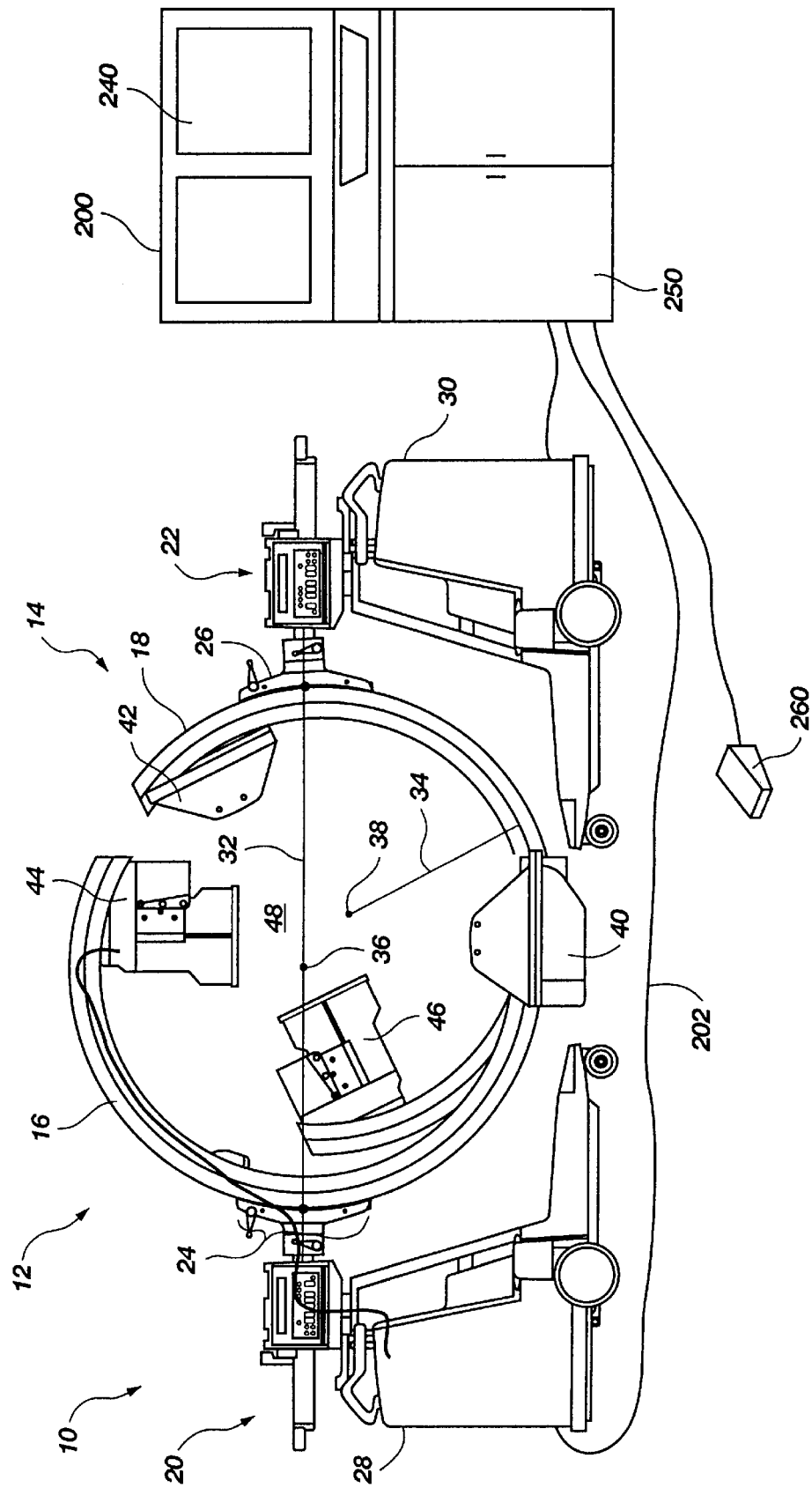
FIG. 1 is a side elevational view of a preferred embodiment of the mobile, bi-planar imaging system of the present invention.

A preferred embodiment in accordance with the present invention is illustrated in FIG. 1 wherein is shown a mobile, bi-planar X-ray apparatus, generally designated at 10. The apparatus 10 has a first imaging system 12 and a second imaging system 14. The imaging systems 12 and 14 have first and second C-arms 16 and 18, respectively, terminating in opposing upper and lower distal ends. The C-arms 16 and 18 preferably have a uniformly circular C-shape, but may alternatively comprise any arc-shaped member.

The C-arms 16 and 18 are held in a suspended position by first and second support structures or carriage, generally designated at 20 and 22, respectively, which includes first and second support arms 24 and 26 mounted upon first and second wheeled bases 28 and 30. The support arms 24 and 26 provide for rotational movement of the C-arms 12 and 14 about an axis of lateral rotation 32 and 34.

The wheeled bases 28 and 30 enables transport of the C-arms 12 and 14 from a first location to a second location. It is often highly advantageous to be able to move X-ray equipment from one room to another conveniently. The mobile nature of the apparatus 10 as provided by the wheeled bases 28 and 30 offers the advantage of increased access by patients in many different rooms of a hospital, for example.

The support arms 24 and 26 are slidably mounted to the outer circumference of the C-arms 12 and 14 and the support structures 20 and 22 include structure and mechanisms necessary to enable selective, sliding orbital motion of the C-arms about an axis of orbital rotation 36 and 38 to a selected position. The axis 36 and 38 preferably coincides with a center of curvature of the C-arms 12 and 14 and with the axis of lateral rotation 30 and 32. It will be appreciated that the sliding orbital motion causes the C-arms 12 and 14 to move through various points of attachment to the support arms 24 and 26. The support structures 20 and 22 further include mechanisms known in the art for laterally rotating the support arms 24 and 26 selectable amounts about an axis of lateral rotation 30 and 32 to a selected lateral position. The combination of sliding orbital motion and lateral rotation enables manipulation of the C-arms in two degrees of freedom, i.e. about two perpendicular axes. This provides a kind of spherical quality to the movability of the C-arms 12 and 14—the sliding orbital motion and lateral rotation enable an X-ray source coupled to the C-arm to be moved to substantially any latitude/longitude point on a lower hemisphere of an imaginary sphere about which the C-arm is moveable.

The imaging systems 12 and 14 include first and second X-ray sources 40 and 42 and first and second image receptors 44 and 46 as known generally in the X-ray diagnostic art, mounted upon opposing locations, respectively, on the C-arms 12 and 14. The first X-ray source 40 and the first image receptor 44 are referred to collectively as the first imaging system 12. Likewise, the second X-ray source 42 and the second image receptor 46 are referred to collectively as the second imaging system 14. The image receptors 44 and 46 can be an image intensifiers or the like. The orbital and laterally rotational manipulation of the C-arm enables selective positioning of the imaging systems 12 and 14 with respect to the width and length of a patient located within interior free space 48 of the C-arms 12 and 14. The sliding orbital movement of the C-arms cause the imaging systems 12 and 14 to move along respective arcuate movement paths.

It is preferred that the axis of lateral rotation 32 and 34 pass through the center of curvature 36 and 38 of the C-arms 12 and 14 in a substantially horizontal orientation, although such is not required. As noted above, the C-arms 12 and 14 may embody any suitable arc-shaped member, although a uniformly circular C-arm having a single center of curvature is preferred. However, an arc-shaped member having multiple centers of curvature may be used with the present invention, in which case it is preferred that the axis of lateral rotation 32 and 34 coincide with the center of curvature of the portion of the arc-shaped member to which the support arms 24 and 26 is attached for a given position of the arc-shaped member.

Although applicant has referred to the attachment of the support arms 24 and 26 to the C-arms 12 and 14 as a "point of attachment", it will be appreciated that in practice, the support arm is essentially attached to the C-arm over an area and not a point, although a "point" may be a large area or a small site. The phrase "point of attachment" as used herein shall refer generally to some central point within the area of attachment. The central point of attachment preferably coincides with a geometric centroid of the area of attachment. It is also to be understood that the phrase "slidably mounted" as used herein shall include any suitable mounting of the C-arms 12 and 14 to the support arms 24 and 26 which enables an orbital, circulating-type motion of the C-arms about the axis 36 and 38. The phrase "slidably mounted" is thus not to be limited to literal sliding action but may include stepped advancement achieved with notched structure, geared advancement, or any other suitable advancement means.

Figure 2:
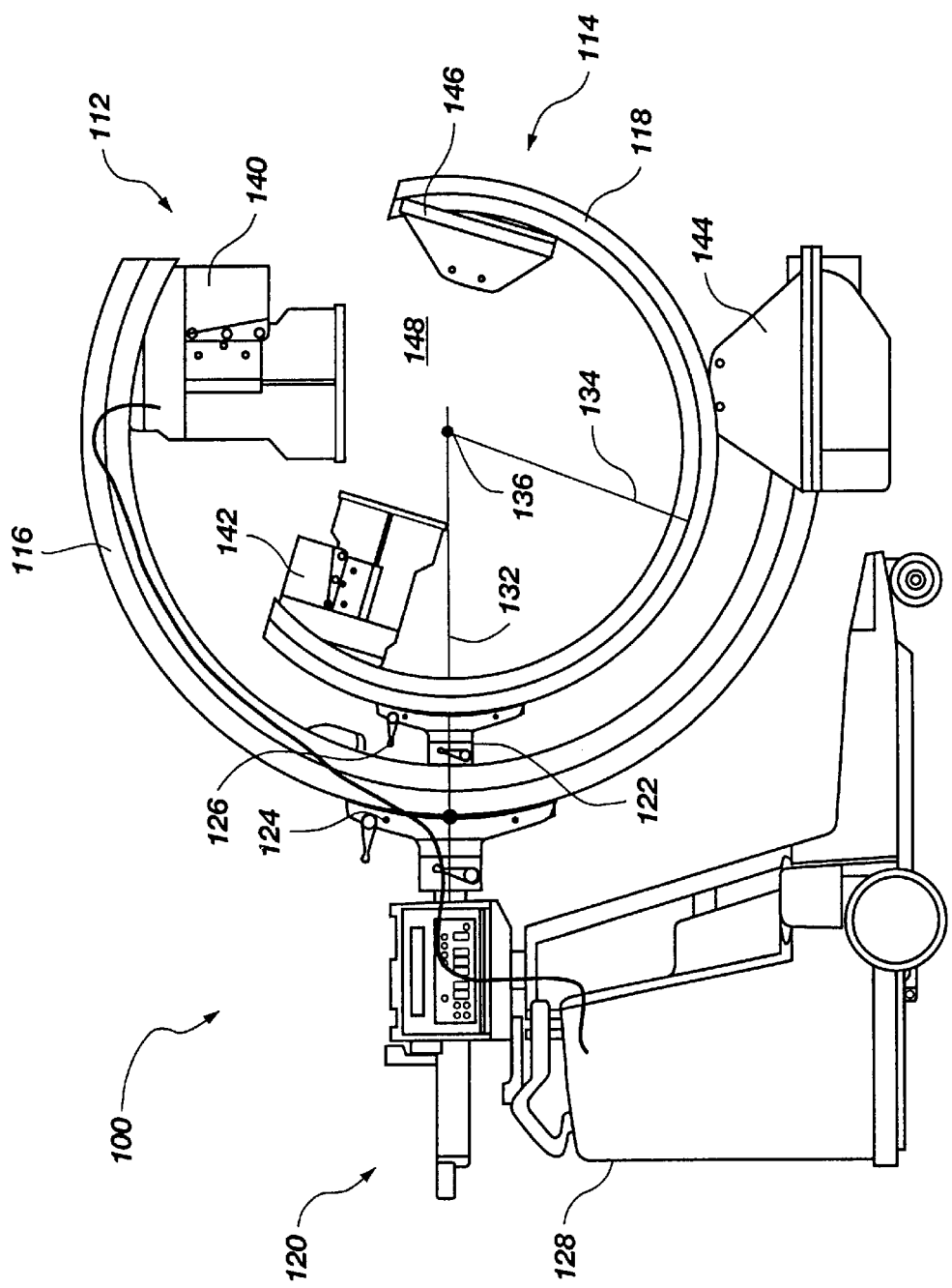
FIG. 2 is a side elevational view of an alternative embodiment of a mobile, bi-planar imaging system of the present invention.

An alternative embodiment in accordance with the present invention is illustrated in FIG. 2 wherein is shown a mobile, bi-planar X-ray apparatus, generally designated at 100. The apparatus 100 has a first imaging system 112 and a second imaging system 114. The imaging systems 112 and 114 have first and second C-arms 116 and 118, respectively, terminating in opposing upper and lower distal ends. The C-arms 116 and 118 preferably have a uniformly circular C-shape, but may alternatively comprise any arc-shaped member.

The first C-arm 116 is held in a suspended position by a support structure or carriage, generally designated at 120, which includes a support arm 124 mounted upon a wheeled base 128. The support arm 124 provides for rotational movement of the C-arm 112 about an axis of lateral rotation 132. The wheeled base 128 enables transport of the C-arms 112 and 114 from a first location to a second location.

The support arm 124 is slidably mounted to the outer circumference of the first C-arm 112 and the support structure 120 includes structure and mechanisms necessary to enable selective, sliding orbital motion of the C-arm about an axis of orbital rotation 136 to a selected position. The support structure 120 further includes mechanisms known in the art for laterally rotating the support arm 124 selectable amounts about an axis of lateral rotation 132.

The second C-arm 118 is held in a suspended position by a support structure 122, which includes a support arm 126 mounted on the first C-arm 116. The support arm 126 provides for rotational movement of the C-arm 118 about an axis of lateral rotation 134. The support arm 126 is slidably mounted to the outer circumference of the second C-arm 118 and the support structure 122 includes structure and mechanisms necessary to enable selective, sliding orbital motion of the C-arm about an axis of orbital rotation 138 to a selected position. The support structure 122 further includes mechanisms known in the art for laterally rotating the support arm 126 selectable amounts about an axis of lateral rotation 132. As shown in FIG. 2, the C-arms 116 and 118 will often share a common axis of orbital rotation 136 and 138. The axis of orbital rotation, however, may be different for each C-arm.

The first C-arm 116 has a larger diameter than the second C-arm 118. In addition, the second C-arm 118 is pivotally and slidably disposed on the first C-arm 116. Thus, the second C-arm 118 may nest within the first C-arm 116.

The imaging systems 112 and 114 include first and second X-ray sources 140 and 142 and first and second image receptors 144 and 146, mounted upon opposing locations, respectively, on the C-arms 112 and 114. The orbital and laterally rotational manipulation of the C-arm enables selective positioning of the imaging systems 112 and 114 with respect to the width and length of a patient located within interior free space 148 of the C-arms 116 and 118. The sliding orbital movement of the C-arms cause the imaging systems 112 and 114 to move along respective arcuate movement paths.

Figure 3:
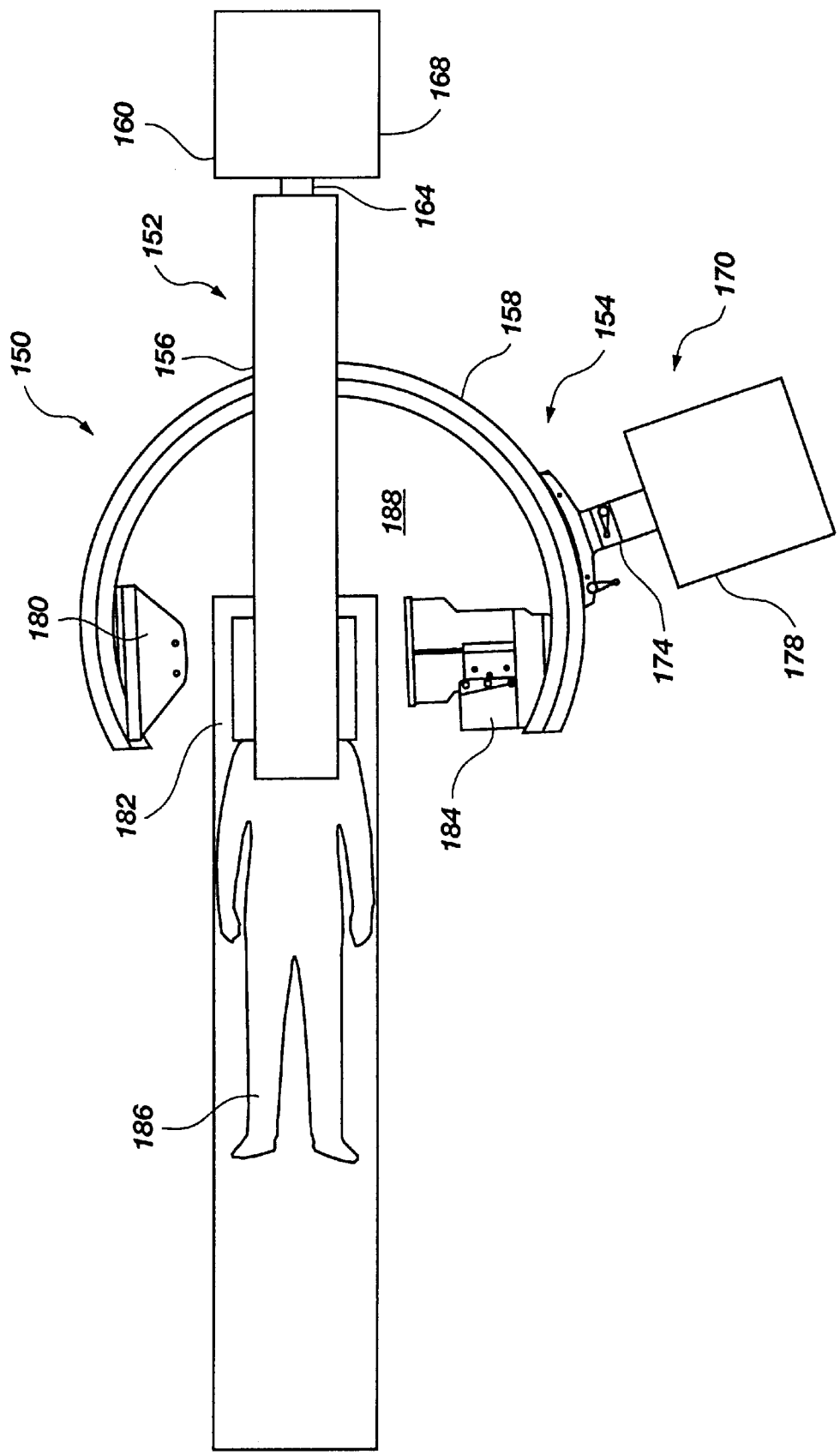
FIG. 3 is a top view of an alternative embodiment of a mobile, bi-planar imaging system of the present invention.

An alternative embodiment in accordance with the present invention is illustrated in FIG. 3 wherein is shown a mobile, bi-planar X-ray apparatus, generally designated at 150. The apparatus 150 has a fi aging system 152 and a second imaging system 154. The imaging systems 152 and 154 have first and second C-arms 156 and 158, respectively, terminating in opposing upper and lower distal ends. The C-arms 156 and 158 preferably have a uniformly circular C-shape, but may alternatively comprise any arc-shaped member.

The first C-arm 156 is held in a suspended position by a support structure or carriage, generally designated at 160, which includes a support arm 164 mounted upon a wheeled base 168. The wheeled base 168 enables transport of the C-arm 156 from a first location to a second location.

The second C-arm 158 is held in a suspended position by a support structure or carriage, generally designated at 170, which includes a support arm 174 mounted upon a wheeled base 178. The wheeled base 178 enables transport of the C-arm 158 from a first location to a second location. Therefore, the apparatus 150 is similar to the apparatus shown in FIG. 1, in that it has two independently movable C-arms.

The first C-arm 156 has a larger diameter than the second C-arm 158. Thus, the second C-arm 158 may be located so that it nests within the first C-arm 156. Therefore, the apparatus 150 is similar to the apparatus shown in FIG. 2, in that it has two different sized C-arms.

The imaging systems 152 and 154 include first and second X-ray sources 180 and 182 and first and second image receptors 184 (the second image receptor not shown in FIG. 3), mounted upon opposing locations, respectively, on the C-arms 156 and 158. The orbital and laterally rotational manipulation of the C-arms enables selective positioning of the imaging systems 152 and 154 with respect to the width and length of a patient 186 located within interior free space 188 of the C-arms 156 and 158 while still giving access to the patient 186, as shown in FIG. 3.

Figure 4:
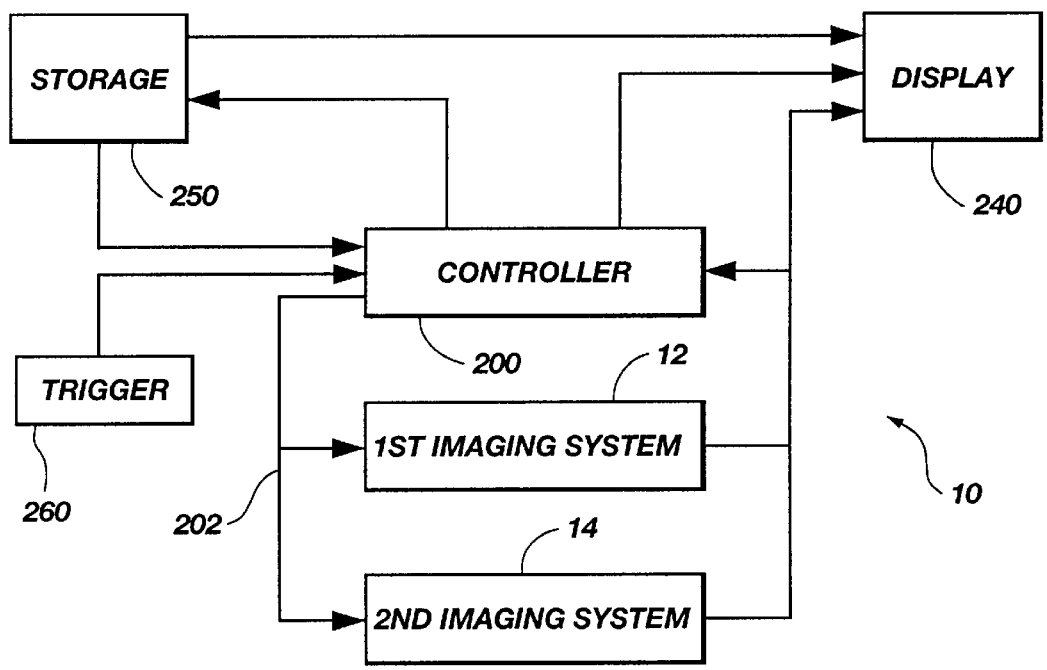
FIG. 4 is a block diagram of a preferred embodiment of the mobile, bi-planar imaging system of the present invention.

As illustrated in FIGS. 1 and 4, the apparatus 10 has a controller 200 in addition to the first and second imaging systems 12 and 14. The controller 200 causes the first and second imaging systems 12 and 14 to operate and produce images. The two imaging systems will often be positioned to obtain a bi-planar image of single object. Thus, the imaging systems will often share a common axis or be positioned such that the X-ray beams produced by the X-ray sources cross. It is undesirable to operate the two imaging systems simultaneously because the crossing X-ray beams may cause the resulting image to be blurred and the patient is exposed to increased levels of radiation. Therefore, the controller causes the imaging systems to alternate operation.

The controller 200 is coupled to each of the first and second imaging systems by control wires 202. The controller may be coupled to the imaging system electrically or by any other appropriate means including fiber optics, infra red signals, and the like. The controller 200 alternately triggers the first and second imaging systems by sending a triggering pulse to each system alternately. The controller may be separate from the imaging systems, as shown in FIG. 1.

Figure 5:
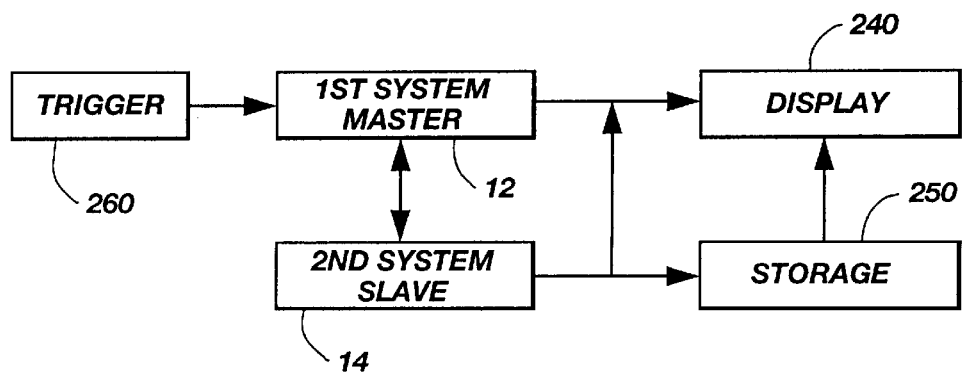
FIG. 5 is a block diagram of an alternative embodiment of the mobile, bi-planar imaging system of the present invention.

Alternatively, the imaging systems may be configured in a master/slave relationship, as shown in FIG. 5. The first imaging system 12 is the master and the second imaging system 14 is the slave. The master system sends a triggering pulse to the slave system to cause the slave system to operate.

Figure 6:
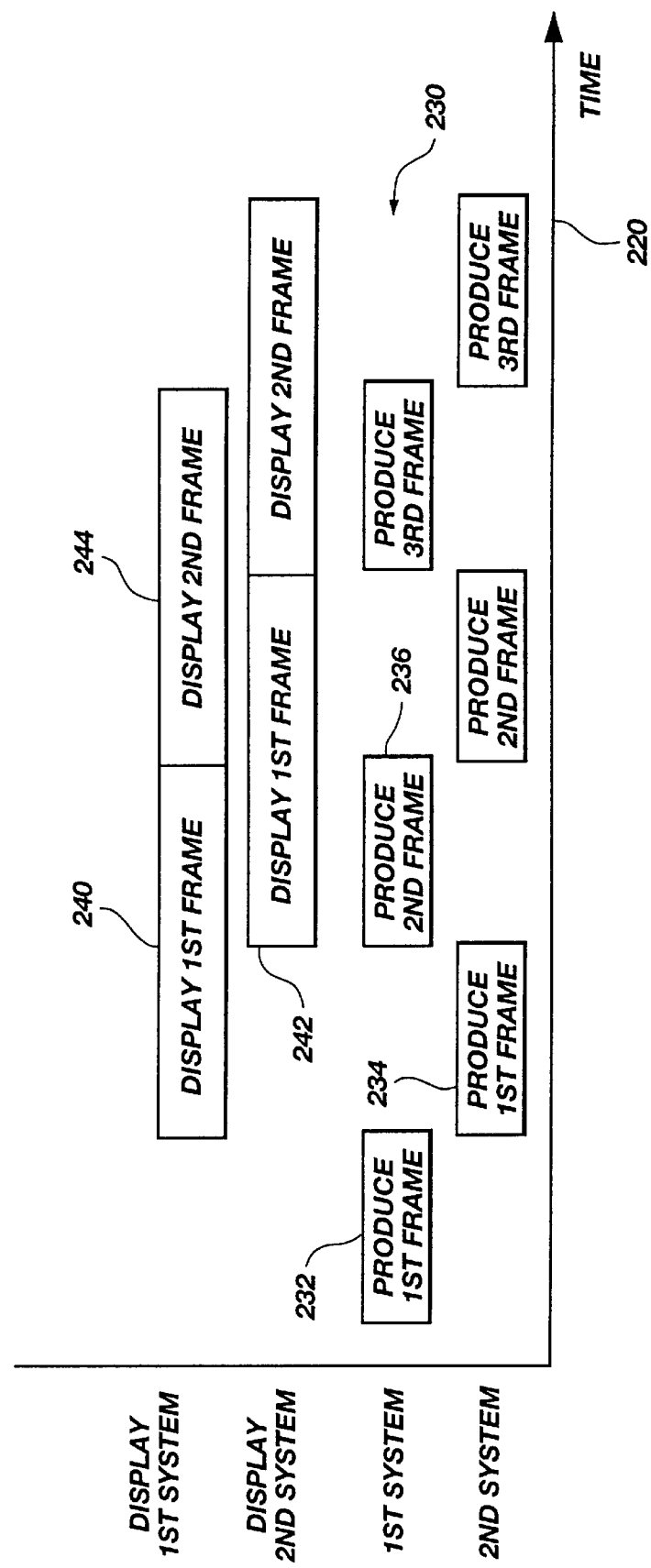
FIG. 6 is a graph showing the operation of the bi-planar imaging system of the present invention.

As illustrated in FIG. 6, the operation of the apparatus is shown in the graph where the horizontal axis 220 represents time and the vertical axis represents the imaging systems and display. The first and second imaging systems 12 and 14 alternately operate to each produce a timewise sequence of successive images, indicated generally at 230. Each image produced by the imaging system defines a frame and each sequence of successive images defines a sequence of successive frames. The first imaging system 12 operates to produce an image defining a first frame 232 for the first system. The second imaging system 14 then operates to produce an image defining a first frame 234 for the second system. The controller 200 alternates the operation by sending a triggering pulse to the systems. Alternatively, the master system sends a triggering pulse to the slave system after it has produced an image. Therefore, the first and second imaging systems 12 and 14 are in communication with each other so that they alternate operation.

As illustrated in FIGS. 1, 4 and 5, the apparatus 10 also has a display 240 coupled to the first and second imaging systems 12 and 14. The display 240 may consist of two separate video monitors, one for each imaging system, as shown in FIG. 1. Alternatively, the display may be a single monitor configured to display the images from both imaging systems. In addition, the imaging systems may send the images through the controller 200, as shown in FIG. 4, or may send the images directly to the display 240, as shown in FIG. 5. Furthermore, the display 240 may be formed integrally with the controller 200, as shown in FIG. 1, or may be separate from the controller and imaging systems.

The display 240 simultaneously displays the images produced by each imaging system 12 and 14. In addition, the display 240 displays the images in real-time, or as they are produced by the imaging systems. Furthermore, the display is continuous. The display 240 displays an image from the first system continuously while the second system operates to produce an image. Likewise, the display displays the image from the second system continuously while the first system operates to produce an image. Therefore, although the imaging systems operate alternately, the images produced are displayed continuously while the other imaging system operates. Referring again to FIG. 6, the first imaging system 12 operates producing an image defining a first frame 232 which is then displayed, as indicated at 240. The display of the first frame 232 from the first system is displayed while the second system operates producing an image defining a first frame 234 which is then displayed, as indicated at 242. The display of the first frame 234 from the second system is displayed while the first system operates producing an image defining a second frame 236 which then replaces the first frame 232 of the first system. This process continues, each system providing a sequence of images or frame that are displayed continuously.

As illustrated in FIGS. 1, 4 and 5, the apparatus 10 also has a storage device 250 coupled to the first and second imaging systems 12 and 14. The storage device 250 stores the images produced by the first and second imaging systems 12 and 14 for later retrieval and viewing. The stored images may be used in post-operative procedures. The imaging systems 12 and 14 may send the images to the storage device 250 through the controller 200, as shown in FIG. 4, or may send the images directly to the storage device 250, as shown in FIG. 5. In addition, the storage device 240 may be formed integrally with the controller 200, as shown in FIG. 1, or may be separate from the controller and imaging systems.

The storage device 250 preferably stores the images in real-time, or as they are produced by the imaging systems. The storage device 250 may also keep track or organize the images so that they may be retrieved and viewed. The storage device delivers the images to the display during playback. The storage device alternates delivers of images between those produced from the first imaging system and those produced from the second imaging system.

The storage device preferably stores the images as digital video on a hard disk drive. Alternatively, the images may be saved on video cassette.

As illustrated in FIGS. 1, 4 and 5, the apparatus 10 also has an external trigger 260. The external trigger 260 starts the apparatus 10. The external trigger 260 may send a trigger pulse to the controller 200, as shown in FIG. 4, or may send a trigger pulse directly to the first imaging system 12, as shown in FIG. 5. The external trigger 260 may be a foot pedal, as shown in FIG. 1.

A presently preferred method for taking bi-planar images includes first and second steps of providing first and second mobile imaging systems for taking images in first and second planes, respectively.

The third step is operating the first imaging system to produce an image in the first plane. The image defines a first frame of the first system. The fourth step is displaying the frame. The frame is preferably displayed continuously while the second system operates as described below. In addition, the frame is preferably stored.

The fifth step is operating the second imaging system to produce an image in the second plane. The image defines a first frame of the second system. The sixth step is displaying the frame. The frame is preferably displayed continuously while the first system operates. In addition, the frame is preferably stored.

The seventh step is repeating steps three through six as desired. The frames produced by the first system are displayed continuously while the second system operates to produce a frame and vis versa.

The final step may be retrieving and displaying the stored frames.

It is to be understood that the described embodiments of the invention are illustrative only, and that modifications thereof may occur to those skilled in the art. Accordingly, this invention is not to be regarded as limited to the embodiments disclosed, but is to be limited only as defined by the appended claims herein.

What is claimed is:

1. A bi-planar fluoroscopic imaging apparatus comprising:
   a first imaging system for producing images in a first plane;
   a second imaging system in communication with the first imaging system, the second imaging system being separate from and independently movable with respect to the first imaging system for producing images in a second plane; and
   a control means coupled to the first and second imaging systems to cause the first and second imaging systems to alternate operation in producing images; and
   wherein the first and second imaging systems communicate in a master and slave relationship where the first imaging system is a master and the second imaging system is a slave and wherein the master imaging system includes the control means to send a trigger pulse after the master imaging system operates to produce an image to the slave imaging system to begin operation of the slave imaging system.

2. The apparatus of claim 1, wherein the control means causes the first and second imaging systems to alternately operate to each produce a series of sequential images; and wherein each image defines a frame and each sequence of successive images defines a sequence of successive frames.

3. The apparatus of claim 2, further comprising a display means coupled to the first and second imaging systems for simultaneously displaying an image produced by each of the first and second imaging systems.

4. The apparatus of claim 3, wherein the first and second imaging systems, control means, and display means are configured to display the images as they are produced by the first and second imaging systems.

5. The apparatus of claim 3, wherein the first and second imaging systems, control means, and display means are configured to display an image from the first system continuously while the second system operates to produce an image and wherein the display means displays the image from the second system continuously while the first system operates to produce an image.

6. The apparatus of claim 3, further comprising a storage means for storing the images as they are produced and for alternating delivery of the images produced from the first and second imaging systems to the display means.

7. The apparatus of claim 6, wherein the first and second imaging systems, control means, and storage means are configured to synchronize delivery of the images to the display means such that the images produced by the first imaging system and the images produced by the second imaging system are displayed simultaneously.

8. The apparatus of claim 6, wherein the storage means is a digital video device and stores the images as real time digital video.

9. The apparatus of claim 6, wherein the storage means is a hard disk drive.

10. The apparatus of claim 6, wherein the storage means is a video cassette.

11. The apparatus of claim 1, wherein the first imaging system has a first C-shaped arm rotatable about a first axis of lateral rotation and orbital about a first axis of orbital rotation orthogonal to the first axis of lateral rotation; and wherein the second imaging system has a second C-shaped arm rotatable about a second axis of lateral rotation different from the first axis of lateral rotation, and orbital about a second axis of orbital rotation different from the first axis of orbital rotation and orthogonal to the second axis of lateral rotation.

12. The apparatus of claim 1, wherein the first imaging system comprises a first X-ray source for producing an X-ray beam, a first image receptor for receiving at least some of the X-ray beam and developing an image, and a first C-shaped arm, the first X-ray source being disposed on one end of the first C-shaped arm, the first image receptor being disposed on the other end of the first C-shaped arm; and wherein the second imaging system comprises a second X-ray source for producing an X-ray beam, a second image receptor for receiving at least some of the X-ray beam, and a second C-shaped arm apart from and independently movable with respect to the first C-shaped arm, the second X-ray source being disposed on one end of the second C-shaped, the second image receptor being disposed on the other end of the second C-shaped arm.

13. The apparatus of claim 12, wherein the first and second imaging system are mobile imaging systems, wherein the first imaging system further comprises a first wheeled base movably disposed on the ground and wherein the first C-shaped arm is movably disposed on the first wheeled base; and wherein the second imaging system further comprises a second wheeled base movably disposed on the ground and wherein the second C-shaped arm is movably disposed on the second wheeled base.

14. The apparatus of claim 12, wherein the first C-shaped arm has a larger diameter than the second C-shaped arm.

15. A bi-planar fluoroscopic imaging apparatus comprising:
   a first mobile imaging system having a first X-ray source and a first image receptor each disposed on opposing ends of a first C-shaped arm for producing images in a first plane, the first imaging system further including a first wheeled base movably disposed on the ground with the first C-shaped arm movably disposed on the first wheeled base;

a second mobile imaging system in communication with the first imaging system, the second imaging system being separate from and independently movable with respect to the first imaging system, the second imaging system having a second X-ray source and a second image receptor each disposed on opposing ends of a second C-shaped arm for producing images in a second plane, the second C-shaped arm being apart from and independently movable with respect to the first C-shaped arm, the second imaging system further including a second wheeled base movably disposed on the ground with the second C-shaped arm movably disposed on the second wheeled base;

a control means coupled to the first and second imaging systems to cause the first and second imaging systems to alternate operation to each produce a series of sequential images; each image defining a frame and each series of sequential images defining a series of sequential frames; and a display means coupled to the first and second imaging systems for simultaneously displaying an image produced by each of the first and second imaging systems as the images are produced such that a first frame from the first system is continuously displayed while the second system operates to produce a first frame and the first frame from the second system is continuously displayed while the first system operates to produce a second frame; and wherein the first and second imaging systems communicate in a master and slave relationship where the first imaging system is a master and the second imaging system is a slave and wherein the master imaging system includes the control means to send a trigger pulse after the master imaging system operates to produce an image to the slave imaging system to begin operation of the slave imaging system.

16. The apparatus of claim 15, wherein the first C-shaped arm rotates about orthogonal first axes of lateral and orbital rotation; and wherein the second C-shaped arm rotates about orthogonal second axes of lateral and orbital rotation different from the first axes of lateral and orbital rotation.

17. The apparatus of claim 15, wherein the first C-shaped arm has a larger diameter than the second C-shaped arm.

18. The apparatus of claim 15, further comprising a storage means for storing the images as they are produced and for alternating delivery of the images produced from the first and second imaging systems to the display means.

19. The apparatus of claim 18, wherein the first and second imaging systems, control means, and storage means are configured to synchronize delivery of the images to the display means such that the images produced by the first imaging system and the images produced by the second imaging system are displayed simultaneously.

20. A bi-planar fluoroscopic imaging apparatus comprising:

a first imaging system having a first X-ray source and a first image receptor each disposed on opposing ends of a first C-shaped arm for producing images in a first plane, the first C-shaped arm rotating about a first axis of lateral rotation;

a second imaging system in communication with the first imaging system, the second imaging system having a second X-ray source and a second image receptor each disposed on opposing ends of a second C-shaped arm for producing images in a second plane, the second C-shaped arm having a smaller diameter than the first C-shaped arm and being pivotally coupled to the second C-shaped arm such that the second C-shaped arm may nest within the first C-shaped arm, the second C-shaped arm rotating about a second axis of lateral rotation independently of the first C-shaped arm; and a control means coupled to the first and second imaging systems to cause the first and second imaging systems to alternate operation; and wherein the first and second imaging systems communicate in a master and slave relationship where the first imaging system is a master and the second imaging system is a slave and wherein the master imaging system includes the control means to send a trigger pulse after the master imaging system operates to produce an image to the slave imaging system to begin operation of the slave imaging system.

21. The apparatus of claim 20, further comprising display means coupled to the first and second imaging systems for simultaneously displaying an image produced by each of the first and second imaging systems as the images are produced such that a first frame from the first system is continuously displayed while the second system operates to produce a first frame and the first frame from the second system is continuously displayed while the first system operates to produce a second frame.

* * * * *